(12) United States Patent
Cao et al.

(10) Patent No.: US 7,831,304 B2
(45) Date of Patent: Nov. 9, 2010

(54) METHOD FOR DETERMINING OVERSENSING IN AN IMPLANTABLE DEVICE

(75) Inventors: Jian Cao, Shoreview, MN (US); Jeffrey M. Gillberg, Coon Rapids, MN (US); Maneesh Shrivastav, Minneapolis, MN (US); Scott R. Stanskaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1076 days.

(21) Appl. No.: 11/537,171

(22) Filed: Sep. 29, 2006

(65) Prior Publication Data

US 2008/0082014 A1 Apr. 3, 2008

(51) Int. Cl.
*A61N 1/36* (2006.01)
(52) U.S. Cl. .......................................... 607/27; 600/509
(58) Field of Classification Search ...................... 607/28
See application file for complete search history.

(56) References Cited

U.S. PATENT DOCUMENTS

| | | | |
|---|---|---|---|
| 3,940,692 A | 2/1976 | Neilson | |
| 4,854,327 A | 8/1989 | Kunig | |
| 5,117,824 A | 6/1992 | Keimel et al. | |
| 5,339,820 A | 8/1994 | Henry et al. | |
| 5,354,316 A | 10/1994 | Keimel | |
| 5,545,186 A | 8/1996 | Olson et al. | |
| 5,564,430 A | 10/1996 | Jacobson et al. | |
| 6,112,119 A | 8/2000 | Schuelke et al. | |
| 6,393,316 B1 | 5/2002 | Gillberg et al. | |
| 7,024,243 B1 | 4/2006 | Bornzin et al. | |
| 7,027,858 B2 | 4/2006 | Cao et al. | |
| 7,248,921 B2 * | 7/2007 | Palreddy et al. | 607/5 |
| 2004/0015197 A1 * | 1/2004 | Gunderson | 607/27 |
| 2004/0230233 A1 | 11/2004 | Gunderson et al. | |
| 2005/0182334 A1 | 8/2005 | Korzinov et al. | |
| 2006/0116732 A1 | 6/2006 | Gunderson et al. | |
| 2006/0224075 A1 | 10/2006 | Gunderson et al. | |
| 2006/0235476 A1 | 10/2006 | Gunderson et al. | |

* cited by examiner

*Primary Examiner*—Carl H Layno
*Assistant Examiner*—Jeremiah T Kimball
(74) *Attorney, Agent, or Firm*—Michael C. Soldner (57) ABSTRACT

An implantable medical device system and method detect oversensing of cardiac signals. A cardiac signal including first events and second events is acquired. Cardiac events are sensed in response to the cardiac signal crossing a first threshold. A filtered cardiac signal is determined from the sensed cardiac signal, and a second threshold is determined from the filtered cardiac signal. A sensed cardiac event is classified either as a first event when the sensed cardiac event corresponds to a filtered cardiac signal peak crossing the second threshold or a second event when the sensed cardiac event corresponds to a filtered cardiac signal peak being less than the second threshold. Classification of sensed cardiac events as second events is used in determining oversensing.

29 Claims, 7 Drawing Sheets

METHOD FOR DETERMINING OVERSENSING IN AN IMPLANTABLE DEVICE

TECHNICAL FIELD

The invention relates generally to implantable medical devices and, in particular, to a method for determining oversensing of electrical signals in an implantable medical device.

BACKGROUND

Implantable cardiac stimulation devices, such as pacemakers and cardiovertor defibrillators, generally rely on cardiac electrogram (EGM) signals for determining a cardiac rhythm and delivering stimulation therapies as needed.

For example, R-waves are sensed from EGM signals for detecting R-R intervals which are used in detecting and classifying a number of arrhythmias, including ventricular fibrillation (VF) and tachycardia. Oversensing of other cardiac or non-cardiac signals is avoided. Automatic threshold adjustments or increased blanking intervals can be used for preventing oversensing of T-waves, which follow R-waves and are typically lower in amplitude. It is desirable to prevent T-wave oversensing from reducing the sensitivity and accuracy of rhythm detection based on R-wave sensing.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
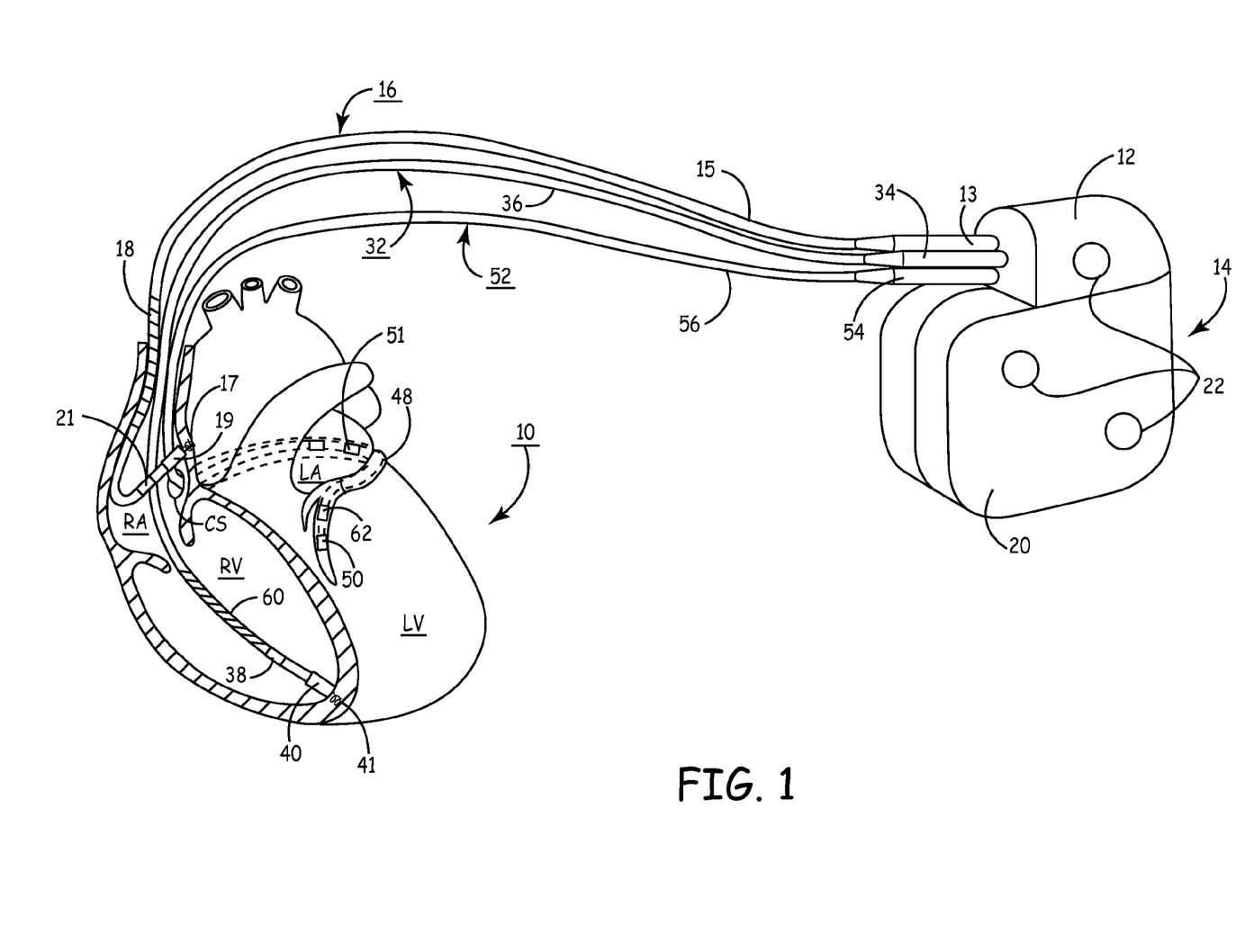
FIG. 1 depicts an implantable, cardiac stimulation device embodied as an implantable cardiovertor defibrillator (ICD), in which methods described herein may be implemented.

FIG. 1 depicts an implantable, cardiac stimulation device embodied as an implantable cardiovertor defibrillator (ICD) 14, in which methods described herein may be implemented. Various embodiments of the invention may be implemented in numerous types of implantable medical devices which include sensing of cardiac signals, such as pacemakers, ECG monitors, and hemodynamic monitors. ICD 14 is provided for sensing intrinsic heart activity and delivering cardiac stimulation pulses in the form of pacing, cardioversion or defibrillation therapy, as appropriate, to one or more heart chambers.

ICD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect ICD 14 with the RA, the RV and the LV, respectively. Each lead has at least one electrical conductor and pace/sense electrode. A remote indifferent can electrode is formed as part of the outer surface of the ICD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using a fixation member 17. RA lead 16 is formed with a connector 13 fitting into a connector bore of ICD connector block 12 for electrically coupling RA tip electrode 19 and RA ring electrode 21 to ICD circuitry housed within housing 20 via insulated conductors extending within lead body 15. RA tip electrode 19 and RA ring electrode 21 may be used in a bipolar fashion, or in a unipolar fashion with ICD housing 20, for achieving RA stimulation and sensing of RA electrogram (EGM) signals. RA lead 16 is also provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, is fixed in place in the RV apex by a distal fixation member 41. RV lead 32 also carries a high-voltage coil electrode 60 for use in cardioverting and defibrillating heart 10. RV lead 32 is formed with a connector 34 fitting into a corresponding connector bore of ICD connector block 12. Connector 34 is coupled to electrically insulated conductors within lead body 36 and connected with distal tip electrode 40, ring electrode 38 and coil electrode 60.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of ICD connector block 12 to provide electrical coupling of conductors extending from electrodes 50 and 62 within lead body 56 to ICD internal circuitry.

In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, ICD 14 may include one or more subcutaneous cardiac sensing electrodes 22 formed as uninsulated portions of the ICD housing 20 or included in the connector block 12. While a particular ICD system with associated leads and electrodes is illustrated in FIG. 1, numerous implantable cardiac monitoring, pacemaker and ICD system configurations are possible, which may include one or more leads deployed in transvenous, subcutaneous, or epicardial locations The lead and electrode arrangements will depend on the particular application. Embodiments of the invention may also include subcutaneous cardiac monitor, pacemaker or ICD systems in which electrodes are formed as a part of the device housing and/or carried by subcutaneous leads.

ICD 14 is shown as a multi-chamber device capable of sensing and stimulation in three or all four heart chambers. It is understood that ICD 14 may be modified to operate as a single chamber device or dual chamber device. Furthermore, it is recognized that embodiments of the present invention may be practiced in a single chamber, dual chamber or multi-chamber implantable cardiac pacemaker that does not include cardioversion and defibrillation functions, or in cardiac monitoring devices that do not include therapy delivery functions.

Figure 2:
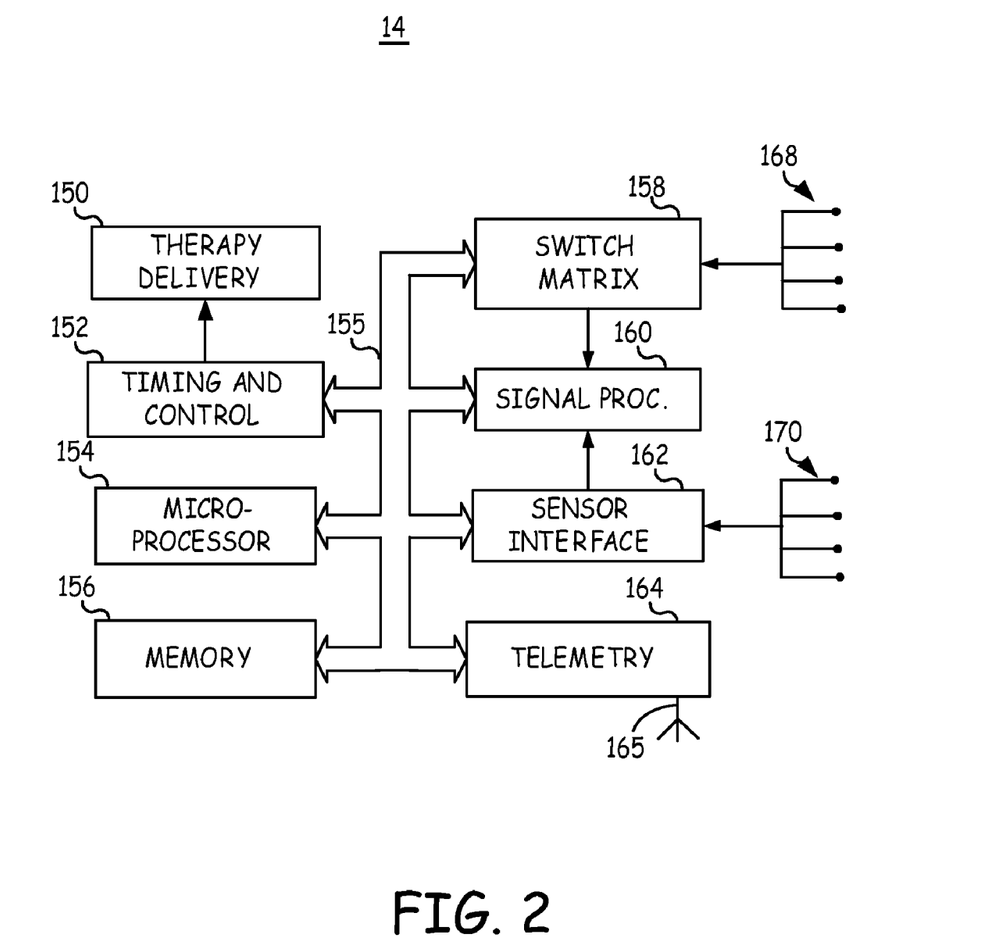
FIG. 2 is a functional block diagram showing some of the components typically included in an implantable cardiac stimulation device such as the ICD shown in FIG. 1.

FIG. 2 is a functional block diagram showing some of the components typically included in an implantable cardiac stimulation device such as the ICD 14 shown in FIG. 1. ICD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 10 via a data/address bus 155. ICD 14 includes therapy delivery module 150 for delivering electrical stimulation therapies, such as cardiac pacing therapies and arrhythmia therapies including cardioversion/defibrillation shocks, under the control of timing and control 152. Therapy delivery module 150 is typically coupled to two or more electrode terminals 168 via a switch matrix 158. Switch matrix 158 is used for selecting which electrodes and corresponding polarities are used for delivering electrical stimulation pulses.

Cardiac electrical signals are sensed for determining when an electrical stimulation therapy is needed and in controlling a stimulation mode and the timing of stimulation pulses. Electrodes used for sensing and electrodes used for stimulation may be selected via switch matrix 158. When used for sensing, electrode terminals 168 are coupled to signal processing circuitry 160 via switch matrix 158. Signal processor 160 includes sense amplifiers and may include other signal conditioning circuitry and an analog to digital converter. Electrical signals may then be used by microprocessor 154 for detecting physiological events, such as detecting and discriminating cardiac arrhythmias. Signal processing circuitry 160 may include event detection circuitry generally corresponding to R-wave detection circuitry as disclosed in U.S. Pat. No. 5,117,824 (Keimel, et al.), hereby incorporated herein by reference in its entirety.

Arrhythmia detection algorithms may be implemented for detecting ventricular tachycardia (VT), ventricular fibrillation (VF) as well as atrial arrhythmias such as atrial fibrillation (A FIB). Ventricular event intervals (R-R intervals) sensed from the EGM signals are commonly used for detecting ventricular arrhythmias. Additional information obtained such as R-wave morphology, slew rate, other event intervals (P-R intervals) or other sensor signal information may be used in detecting, confirming or discriminating an arrhythmia. Reference is made to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals, all of which patents are incorporated herein by reference in their entirety.

In one detection scheme, programmable detection interval ranges designate the range of sensed event intervals indicative of a tachycardia and may be defined separately for detecting slow tachycardia, fast tachycardia and fibrillation. Sensed event intervals falling into defined detection interval ranges are counted to provide a count of tachycardia intervals. A programmable number of intervals to detect (NID) defines the number of tachycardia intervals occurring consecutively or out of a given number of preceding event intervals that are required to detect tachycardia. A separately programmed NID may be defined for detecting slow and fast tachycardia and fibrillation. In addition to the interval ranges and NID criteria, rapid onset criterion and rate stability criterion may also be defined for use in tachycardia detection schemes. Furthermore, a combined count of tachycardia and fibrillation intervals may be compared to a combined count threshold and, according to predefined criteria, used in detecting fibrillation or slow or fast tachycardia.

In addition to event interval information, the morphology of the EGM signal may be used in discriminating heart rhythms, for example as described in the above-incorporated '316 Gillberg patent. According to one embodiment of the invention, digitized EGM signals are provided to microprocessor 154 for waveform analysis according to an implemented morphology or template matching algorithm. Morphology analysis may be used in conjunction with event interval analysis to improve the sensitivity and specificity of arrhythmia detection methods.

In response to an arrhythmia detection, a programmed arrhythmia therapy is delivered by therapy delivery module 150 under the control of timing and control 152. A description of high-voltage output circuitry and control of high-voltage shock pulse delivery is provided in the above-incorporated '186 Olson patent. Typically, a tiered menu of arrhythmia therapies are programmed into the device ahead of time by the physician and stored in memory 156. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold.

In the event that fibrillation is identified, high frequency burst stimulation may be employed as the initial attempted therapy. Subsequent therapies may be delivery of high amplitude defibrillation pulses, typically in excess of 5 joules. Lower energy levels may be employed for cardioversion. The defibrillation pulse energy may be incremented in response to failure of an initial pulse or pulses to terminate fibrillation.

ICD 14 may additionally or alternatively be coupled to one or more physiological sensors via physiological sensor terminals 170. Physiological sensors may include pressure sensors, accelerometers, flow sensors, blood chemistry sensors, activity sensors or other physiological sensors known for use with implantable cardiac stimulation devices. Physiological sensors may be carried by leads extending from ICD 14 or incorporated in or on the ICD housing.

The operating system includes associated memory 156 for storing a variety of programmed-in operating mode and parameter values that are used by microprocessor 154. The memory 156 may also be used for storing data compiled from sensed EGM and physiological signals and/or relating to device operating history for telemetry out on receipt of a retrieval or interrogation instruction.

ICD 14 further includes telemetry circuitry 164 and antenna 165. Programming commands or data are transmitted during uplink or downlink telemetry between ICD telemetry circuitry 164 and external telemetry circuitry included in a programmer or monitoring unit.

Figure 3:
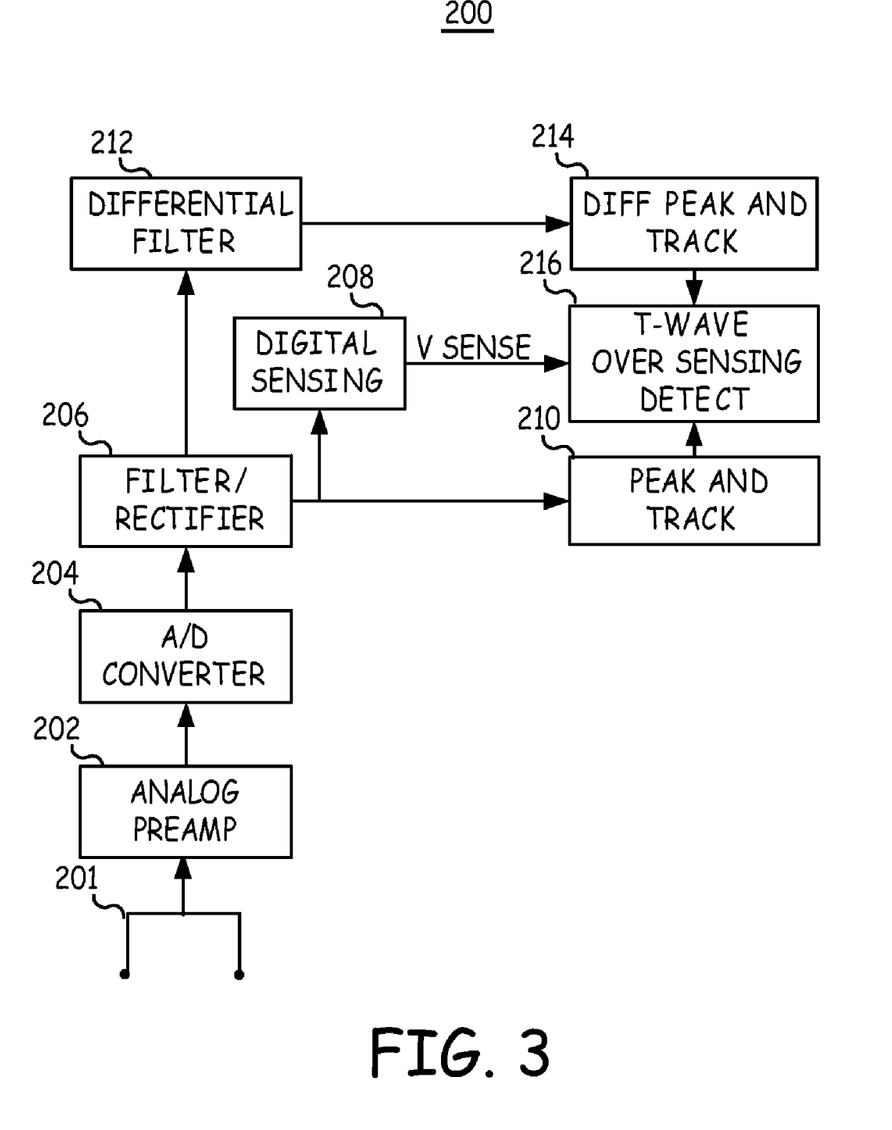
FIG. 3 is a functional block diagram of signal processing components included in an implantable medical device for identifying T-wave oversensing.

FIG. 3 is a functional block diagram of signal processing components included in an implantable medical device such as ICD 14 for identifying T-wave oversensing. For example, the functional signal processing components shown in FIG. 3 may be included in signal processing module 160 of ICD 14 shown in FIG. 2. The signal processing module 200 shown in FIG. 3 includes an analog preamplifier 202 for receiving a cardiac EGM or subcutaneous ECG signal (collectively referred to hereinafter as "EGM signal") from a sensing electrode pair 201 (either unipolar or bipolar pair) selected from any of the available electrodes. The analog signal output from preamplifier 202 is converted to a digital signal by A/D converter 204. The digital EGM signal is provided as input to a digital filter/rectifier 206 which provides a filtered and rectified signal to a digital sensing module 208. The digital sensing module 208 senses ventricular events from the filtered and rectified digital EGM signal. Ventricular sensed events may be detected based on the EGM signal crossing a primary sensing threshold. The primary sensing threshold is typically determined as an automatically adjusted threshold on a beat-by-beat basis, e.g. as described in the '824 Keimel patent.

A ventricular (V) sense signal is provided as output from the digital sensing module 208 upon each primary sensing threshold crossing of the filtered, rectified digital EGM signal. The filtered and rectified digital EGM signal from filter/rectifier 206 is further provided to a peak and track module 210. Peak and track module 210 provides a peak tracking output signal corresponding to signal peaks detected on the filtered and rectified EGM signal.

The filtered, rectified digital signal output from filter/rectifier 206 is further provided to a differential filter 212. Differential filter 212 performs differential filtering of the filtered, rectified EGM and provides the differential filtered EGM to a second peak and track module 214. In one embodiment, the differential filtering is performed by subtracting a previous digital signal sample from a current digital signal sample. Mathematically, $y(n)=x(n)-x(n-1)$ where $y(n)$ is the nth point of the differential filtered signal, $x(n)$ is the current digital signal sample from the filtered, rectified digital EGM signal, and $x(n-1)$ is the previous digital signal sample from the filtered, rectified digital EGM signal. In a differential filtered EGM signal the T-wave signals are diminished in amplitude relative to the higher-frequency R-wave signals. Other high pass or band pass filtering methods may be performed on the filtered, rectified digital EGM signal to obtain a signal wherein the relatively lower frequency T-wave signals are more distinguishable from the higher frequency R-waves. Differential filter 212 may therefore be embodied as other types of high pass or band pass filters. The sampling rate for the digital signal can be 1024 Hz, 512 Hz, 256 Hz, etc. The input to the differential filter 212 can also be any unfiltered or filtered signal directly from the A/D converter 204.

The outputs of the digital sensing module 208 (V sense signals), the peak and track module 210 and the differential signal peak and track module 214 are provided as input to T-wave oversensing detection module 216. T-wave oversensing detection module 216 performs algorithms for determining if T-wave oversensing is occurring. If T-wave oversensing is occurring, a cardiac rhythm detected based on V sense signals may be rejected in response to determining T-wave oversensing. A therapy to be delivered by the IMD or other operations of the IMD may be altered or adjusted in response to T-wave oversensing determination. T-wave oversensing detection module 216 may be implemented in software and/or firmware, and/or hardware.

Figure 4:
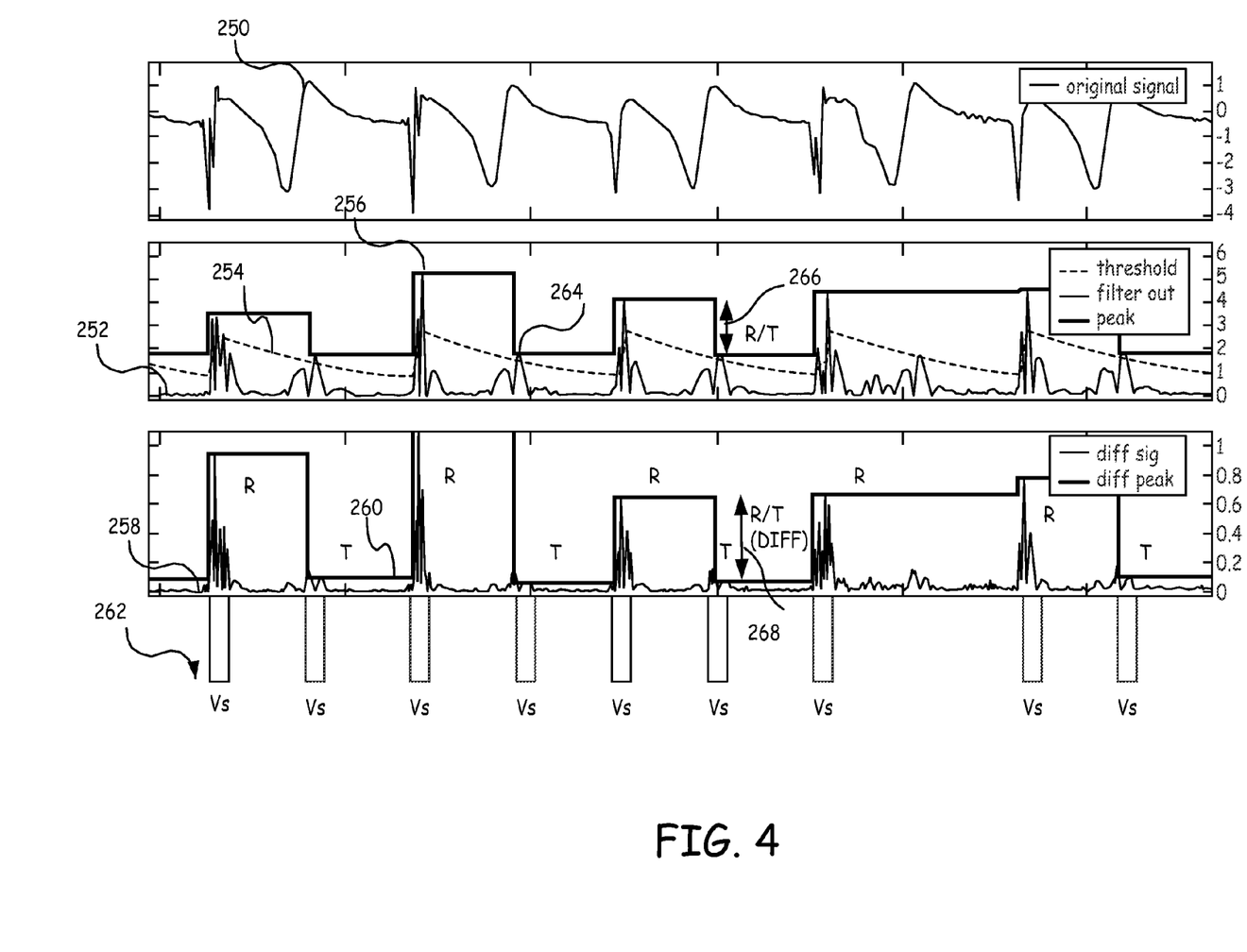
FIG. 4 is a graph illustrating various signal processing functions performed by the signal processing module shown in FIG. 3.

FIG. 4 is a graph illustrating various signal processing functions performed by the signal processing module 200 shown in FIG. 3. An analog EGM signal 250 is shown in the uppermost plot. The analog EGM signal 250 is provided to an A/D converter 204 and a filter/rectifier 206 (both shown in FIG. 3) to produce the filtered, rectified EGM signal 252. A V sense signal 262 is generated each time the filtered, rectified signal 252 crosses an auto-adjusted, primary sensing threshold 254. As can be seen in FIG. 4, some T-waves 264 of the filtered, rectified EGM signal 252 cross the auto-adjusted, primary sensing threshold 254, resulting in V sense signals 262 which do not correspond to R-waves. The filtered, rectified EGM signal 252 is provided to a peak and track module 214 (FIG. 3) which produces the peak tracking signal 256. While FIG. 4 illustrates intrinsic sensed R-waves and sensed T-waves, it will be appreciated by one having skill in the art that the methods described herein may equally be applied to evoked R-waves and T-waves following pacing pulses.

The filtered, rectified EGM signal 252 is further provided to a differential filter 212 (FIG. 3) to produce the differential filtered EGM signal 258. Peak tracking signal 260 is provided as output from a differential EGM peak and track module 214 (FIG. 3). As can be seen by comparing the R/T ratio 266 of the filtered, rectified EGM 252 to the R/T (DIFF) ratio 268 of the differential filtered EGM 258, the differential EGM signal provides an enhanced difference between the amplitudes of R-waves and T-waves. The V sense signals 262, the filtered, rectified EGM peak tracking signal 256, and the differential filtered EGM peak tracking signal 260 are used by T-wave oversensing detection module 216 (FIG. 3).

Figure 5:
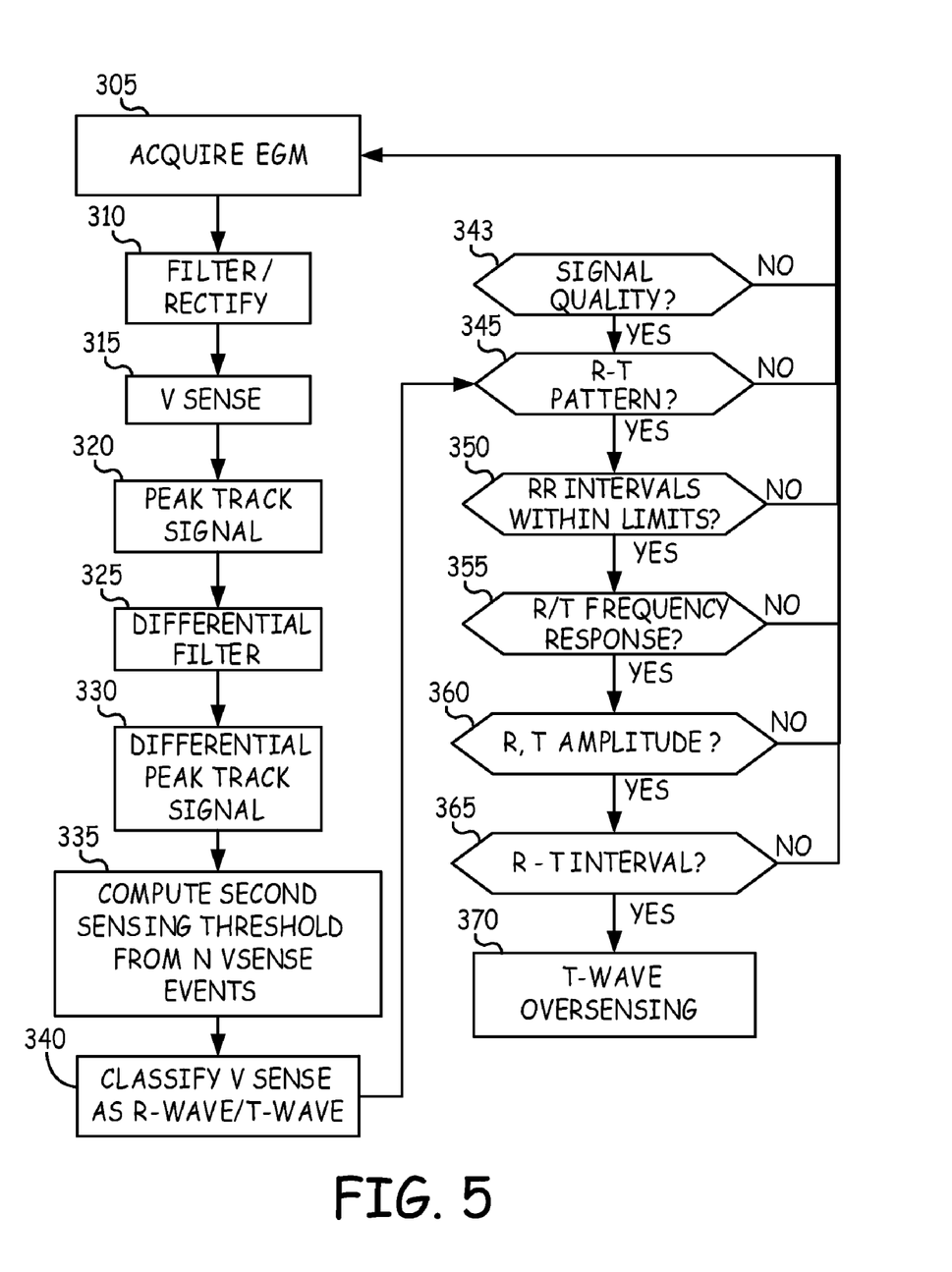
FIG. 5 is a flow chart of a method for determining T-wave oversensing.

FIG. 5 is a flow chart of a method for determining T-wave oversensing. Flow chart 300 is intended to illustrate the functional operation of the device, and should not be construed as reflective of a specific form of software, or firmware or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At step 305, analog EGM signals are acquired via selected sensing electrodes. At block 310, the analog EGM signal is digitized, filtered and rectified as described in conjunction with FIG. 3 and 4. A V sense signal is generated upon each primary sensing threshold crossing of the filtered, rectified EGM. A peak tracking signal is determined from the filtered, rectified EGM at block 320.

The filtered, rectified EGM is filtered a second time at block 325 to enhance the amplitude difference between R-waves and T-waves, for example using a differential filtering method as described previously. At block 330, a peak tracking signal of the differential filtered EGM is determined.

At block 335, a second sensing threshold is computed using the signal peak information determined from the differential filtered signal corresponding to multiple (N) V sense events. Typically, the primary sensing threshold (254 in FIG. 4) is determined from the filtered, rectified EGM and is automatically adjusted in response to R-wave peaks on a beat-by-beat basis. The second sensing threshold determined at block 335 is computed as a function of signal peaks occurring on the differential filtered EGM signal during multiple cardiac cycles, which may include both R-wave peak amplitudes and T-wave peak amplitudes. Specific methods for computing the second threshold will be further described below.

At block 340, the V sense events detected based on primary threshold crossings of the filtered rectified EGM are classified as R-waves and T-waves based on second sensing threshold crossings of the differential filtered EGM. V sense events that correspond in time to differential filtered EGM peaks that cross the second sensing threshold are classified as R-waves. V sense events that correspond in time to differential filtered EGM peaks that do not cross the second sensing threshold are classified as T-waves. As such, V sense events are discriminated into R-waves and T-waves using the second sensing threshold.

Using these classified R-wave and T-wave sensed events, and/or information from the peak tracking signals derived from each of the filtered, rectified EGM and the differential filtered EGM, an algorithm is performed for determining T-wave oversensing. In order to determine if T-wave oversensing is occurring, criteria which correspond to a valid pattern of R-T sensing are defined and applied to the classified R-waves and T-waves and/or peak and track signals.

As will be described herein, determination of T-wave oversensing may be used for rejecting a detected arrhythmia. In some cases, T-wave oversensing may be present but conditions relating to R-wave amplitudes, R-R intervals or other EGM features may not warrant a rejection of an arrhythmia detection. As such, the T-wave oversensing criteria may include conditions for determining when T-wave oversensing evidence is rejected or ignored.

In the embodiment shown in FIG. 5, criteria for determining T-wave oversensing are applied at decision blocks 343 through 370. At block 343, criteria may be applied for eliminating non-cardiac or far-field signal noise or other signal artifacts. For example, in order to determine T-wave oversensing, signal quality criteria may require that no ventricular pace occurs during acquisition of the desired number of V sense events and that the EGM is not clipped (which may be a large non-physiological signal). Criteria may further require that there is no atrial pace event within a certain interval (e.g. 30 ms) of a V sense event. An atrial pace may affect the signal peak of the filtered, rectified signal and make T-wave oversensing determination less reliable. It is recognized that other signal quality criteria may be applied at block 343 before applying other criteria for determining T-wave oversensing.

At block 345, T-wave oversensing criteria relating to determining an R-T pattern of sensed events are tested. The classified R-waves and T-waves are examined to verify an R-T pattern of V sense events. Generally, the number of classified R-waves should be equal to or greater than the number of classified T-waves. Classified R-waves should generally precede classified T-waves. If more V sense events are classified as T-waves than as R-waves, or if runs of T-waves occur without intervening R-waves, an R-T sensing pattern is not evident. If the pattern or number of R-waves and T-waves does not support an R-T sensing pattern, T-wave oversensing is not detected. Method 300 returns to block 305 to acquire the EGM signal and wait for the next V sense event.

At block 350, T-wave oversensing criteria relating to R-R intervals are tested. Initially, R-R intervals used for detecting arrhythmias are measured from V sense events sensed on the filtered, rectified EGM. At block 350, the V sense events classified as R-waves are used to re-determine R-R intervals. If a minimum number of these R-R intervals are within a predetermined range, the R-T sensing pattern verified at block 345 supports a determination of T-wave oversensing. If the minimum number of R-R intervals are not within the predetermined acceptable range, the R-T pattern determined at block 345 as evidence for T-wave oversensing is ignored. The R-R intervals determined at block 350 falling outside an acceptable range do not support a decision to reject an arrhythmia detection, or otherwise alter a decision or operation of the IMD, based on T-wave oversensing. The R-R intervals falling outside of a predetermined acceptable R-R interval range may be evidence of an arrhythmia or other irregularity, despite the presence of T-wave oversensing.

At block 355, criteria relating to the EGM frequency characteristics are tested. The R/T ratio occurring on the filtered, rectified EGM signal is determined from the filtered, rectified EGM peak tracking signal as illustrated in FIG. 4. Likewise, a differential filtered R/T ratio, R/T(DIFF), is determined as the ratio of the signal peaks corresponding to R-waves and the signal peaks corresponding to T-waves on the differential filtered EGM signal. If the frequency components of sensed events in the filtered, rectified EGM correspond to R-waves and T-waves, the relationship of the R/T ratio and the R/T (DIFF) ratio is generally predictable. For example, the R/T ratio will typically be less than the R/T(DIFF) ratio because the difference between R-wave amplitudes and T-wave amplitudes is enhanced by the differential filtering. As such, criteria relating to the relationship of the R/T ratio and the R/T(DIFF) ratio may be applied at block 355 to determine if the frequency response of the differential signal supports a determination of T-wave oversensing. Specific criteria will be further discussed below.

At block 360 T-wave oversensing criteria relating to R-wave and/or T-wave amplitudes are tested. In one embodiment, the amplitudes of the V sense events classified as R-waves should all be similar, e.g. within a predetermined range. A similar requirement may be applied to T-wave amplitudes.

Alternatively, other criteria may be applied such as an R-wave amplitude range, a T-wave amplitude range, etc. The criteria may be defined and tested using either the filtered, rectified EGM signal or the differential filtered EGM signal. If the R-wave and T-wave amplitude criteria are not met, T-wave oversensing is not determined.

At block 365, T-wave oversensing criteria relating to the R-T interval may be applied. The R-T intervals may be measured using the classified R-waves and T-waves. The R-T intervals should all be similar, such as within a predetermined range. If the R-T intervals are highly variable, T-wave oversensing is not determined.

If all T-wave oversensing criteria are met at blocks 345 through 365, T-wave oversensing is detected at block 370. When T-wave oversensing is detected, a T-wave oversensing signal is generated. In a marker channel display, the last V sense event in a series of V sense events used to determine T-wave oversensing may be labeled with a T-wave oversensing indicator.

Figure 6:
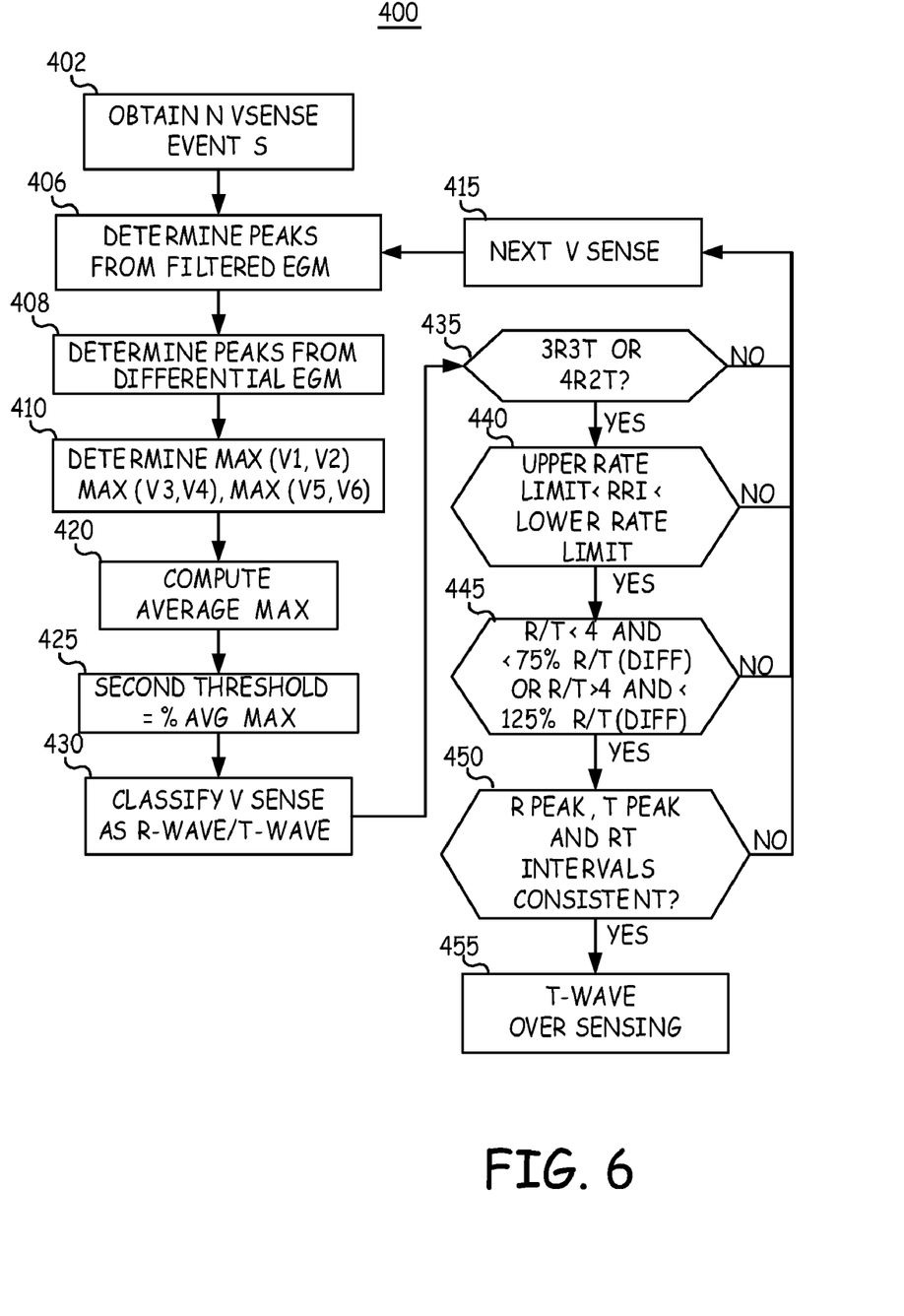
FIG. 6 is a flow chart of a method for determining T-wave oversensing according to specific T-wave oversensing criteria.

FIG. 6 is a flow chart of a method 400 for determining T-wave oversensing according to specific T-wave oversensing criteria. At block 402, a desired number of V sense events are acquired. In one particular embodiment, six V sense events are acquired, however more or less V sense events may be used. The V sense events are detected from the filtered, rectified EGM signal based on a primary sensing threshold crossing as described previously. At block 406, signal peak amplitudes are determined from the filtered, rectified EGM using a peak tracking signal. This peak signal can be obtained during the ventricular sense blanking period (e.g., 120 ms) or a predefined window centered with the ventricular sensed event. At block 408, the signal peak amplitudes are determined from the differential filtered EGM using a peak tracking signal of the differential filtered EGM. The same timing window to obtain the peak signal of the filtered, rectified EGM is used to determine the signal peak of differential signal.

At block 410, the V sense events are selected as pairs of unique, consecutive events. The maximum signal peak amplitude of the differential filtered EGM for each pair of V sense events is determined. For example, if six V sense events are acquired and labeled V1 through V6, the maximum of the differential filtered EGM peak amplitudes corresponding to V1 and V2 is determined, the maximum of V3 and V4 is determined, and so on. Assuming the six V sense events represent an R-T sensing pattern, the peak amplitudes of the R-waves, being greater in amplitude than the T-waves, would be determined from each pair of V sense events at block 410. In other embodiments, the highest M peaks out of N V sense events may be determined.

The maximum differential filtered EGM peak amplitudes determined at block 410 are averaged at block 420. In some embodiments, the largest and/or smallest of the maximums determined at block 410 may be rejected. The second threshold is then computed as a percentage of other function of the average of the maximum peaks. For example, the second threshold may be computed as fifty-percent of the average of the maximum differential filtered EGM peaks.

At block 430 the N V sense events are classified as R-waves and T-waves according to whether the differential filtered EGM peak corresponding to a V sense event crosses the second sensing threshold. At blocks 435 through 450, specific T-wave oversensing criteria are applied to determine if T-wave oversensing is occurring.

At block 435, an R-T sensing pattern is verified by determining if the six V sense events include three R-waves and three T-waves or four R-waves and two T-waves in an alternating pattern. Other patterns or combinations of R-waves and T-waves would not correspond to an R-T sensing pattern. If an R-T sensing pattern is not verified, the next V sense event is obtained at block 435 and blocks 406 through 430 are repeated.

At block 440, the R-R intervals are measured between V sense events classified as R-waves. These R-R intervals are "corrected" R-R intervals using V sense events classified as R-waves based on the second threshold, not the original R-R intervals measured between V sense events, which may be measured and used by arrhythmia detection algorithms which rely on event interval detection criteria. The R-R intervals are compared to a minimum R-R interval corresponding to an upper rate limit and a maximum R-R interval corresponding to a lower rate limit. The minimum R-R interval may correspond to an arrhythmia detection criteria relating to event intervals. In one embodiment, this minimum R-R interval is defined as the maximum of the fibrillation detection interval criteria (FDI), typically about 320 ms and the supraventricular tachycardia (SVT) limit, typically about 240 ms to about 320 ms. In another embodiment, the minimum RR interval corresponds to the ventricular tachycardia detection interval (TDI), typically about 360 ms to about 500 ms. If a predetermined number of the measured R-R intervals fall outside the acceptable range defined by the upper and lower rate limits, the next V sense event is obtained at block 415. R-R intervals outside the acceptable range may not warrant an adjustment of the IMD operation based on T-wave oversensing, even if T-wave oversensing is present.

At block 445, an R/T ratio is determined for the filtered, rectified EGM signal. The R/T ratio is the ratio of R-wave peak amplitudes and T-wave peak amplitudes. The R/T ratio may be determined on a beat-by-beat basis or as the ratio of an average of signal peaks corresponding to classified R-waves and an average of signal peaks corresponding to classified T-waves. A ratio, R/T(DIFF), of the R-wave peak amplitudes and the T-wave peak amplitudes on the differential filtered signal is also determined at block 445. A comparison of the R/T ratio and the R/T(DIFF) ratio will indicate if the difference between the relative amplitudes of higher frequency R-waves and lower frequency T-waves has changed in the differential filtered signal in a way that is consistent with the expected R-wave and T-wave frequency characteristics.

Generally, if the R/T ratio of the filtered, rectified signal is relatively small, the R/T ratio is expected to be less than a fraction of the R/T(DIFF) ratio because the differential filtered signal is expected to enhance the amplitude difference between R-waves and T-waves. For example, in one embodiment, if the R/T ratio is less than 4, then the R/T ratio is expected to be less than approximately 75% of the R/T(DIFF) ratio.

If the R/T ratio of the filtered, rectified signal is relatively large, the R/T ratio may be larger than the R/T(DIFF) ratio, up to some percentage greater than the R/T(DIFF) ratio. In one embodiment, if the R/T ratio is greater than four, then the R/T ratio is expected to be less than approximately 125% of the R/T(DIFF) ratio. If the frequency response of the differential filtered EGM signal is not consistent with a pattern of R-T sensing as verified by a comparison of R/T and R/T(DIFF) at block 445, the next V sense event is obtained at bock 425.

At block 450, the R-wave amplitudes, T-wave amplitudes, and R-T intervals are examined for consistency. This examination may be performed using the filtered, rectified EGM signal or the differential filtered signal based on the signal peaks corresponding to V sense events classified as R-wave and T-waves. If the R-wave peak, T-wave peak and/or R-T interval criteria are not met at block 450, the next V sense event is obtained at block 415. If all classified R-wave peaks are similar, all classified T-wave peaks are similar, and/or all R-T intervals are similar, T-wave oversensing is determined at block 455. All the criteria for verifying the presence of T-wave oversensing has been satisfied. A T-wave oversensing signal may be generated by control circuitry, and the last of the V sense events used in determining T-wave oversensing may be labeled with a T-wave oversensing indicator. If the R-wave peak, T-wave peak and/or R-T interval criteria are not met at block 450, the next V sense event is obtained at block 415.

Figure 7:
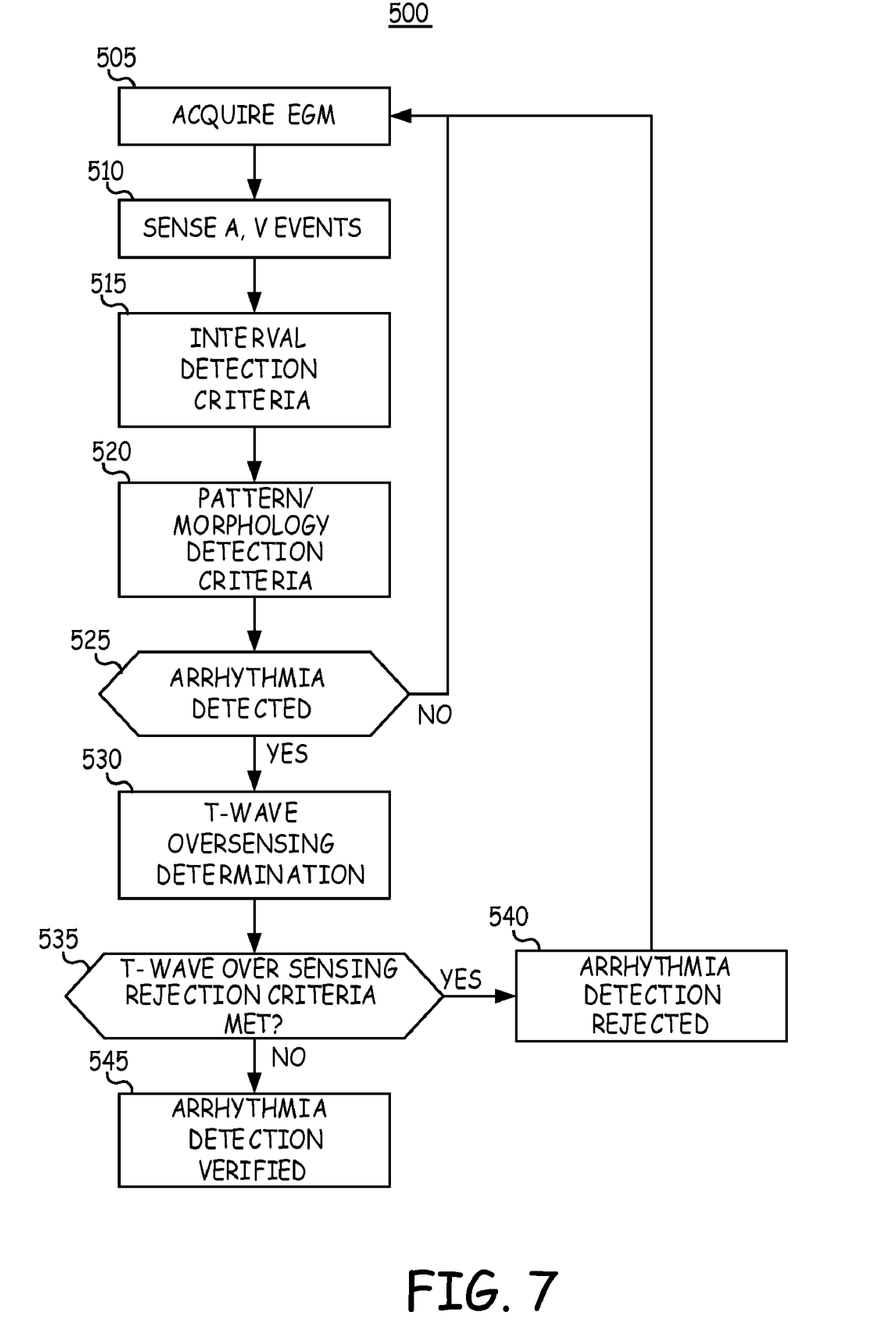
FIG. 7 is a flow chart of an arrhythmia detection method including T-wave oversensing determination.

FIG. 7 is a flow chart of an arrhythmia detection method including T-wave oversensing determination. At block 505, an EGM signal is acquired. At block 510, cardiac events are sensed, which may include both atrial and ventricular sensed events, for use in detecting cardiac arrhythmias. At block 515, cardiac event intervals measured between cardiac events sensed at block 510 are compared to arrhythmia detection criteria based on event intervals. For example, a number of R-R intervals falling into a tachycardia or fibrillation interval detection range out of a given number of cardiac intervals may be required in order to detect a ventricular tachycardia or ventricular fibrillation.

At block 520, other arrhythmia detection or discrimination criteria may be applied. For example, detection/discrimination criteria relating to cardiac event patterns and/or signal morphology may be applied at block 520. It is recognized that any arrhythmia detection algorithms may be used for making an arrhythmia detection based, at least in part, on an EGM signal.

If an arrhythmia is not detected, as determined at decision block 525, method 500 returns to block 505 and continues to acquire EGM signals to monitor for arrhythmias. If an arrhythmia detection is made based on interval, event patterns, and/or EGM morphology criteria, a determination of T-wave oversensing is performed at block 530. The T-wave oversensing determination at block 530 corresponds to the methods described above in conjunction with FIGS. 3 through 6. While the T-wave oversensing determination block 530 is shown in FIG. 7 to follow an arrhythmia detection block 525 based on interval, event pattern and/or morphology of an EGM signal, it is recognized that T-wave oversensing determination may be occurring concurrently with arrhythmia detection algorithms, on a beat-by-beat basis using the desired number of the most recent V sense events. If T-wave oversensing is detected, a T-wave oversensing signal is generated.

At decision block 535, T-wave oversensing rejection criteria are applied. T-wave oversensing rejection criteria define conditions under which an arrhythmia detection, arrhythmia therapy, or other IMD function, would be rejected or otherwise altered based on the presence of T-wave oversensing. In one embodiment, if a predetermined number of V sense events out of a given number of V sense events result in a T-wave oversensing signal, a pending arrhythmia detection is rejected. Any scheduled arrhythmia therapies may be canceled. In a particular example, when the R-R intervals measured according to V sense events (first threshold crossing) are less than a supraventricular tachycardia (SVT) interval limit, a VT or VF episode may be detected according to an arrhythmia detection scheme. If T-wave oversensing rejection criteria are met, the detected VT or VF episode can be rejected even though the V sense intervals are less than the SVT limit. This design allows the T-wave rejection algorithm to operate beyond an SVT limit set by the device. However, the "corrected" R-R intervals measured based on V sense events crossing the second threshold and classified as R-waves (see block 440) should still be greater than the SVT limit in order for T-wave oversensing determination to be made and T-wave oversensing rejection criteria to be met. If the corrected R-R intervals are less than the SVT limit, the T-wave rejection criteria will not be met, and the T-wave oversensing criteria will not override the VTNF detection.

Any rhythm detection and discrimination algorithms relying on V sense events may include T-wave oversensing determination methods as taught herein for verifying appropriate cardiac event sensing. While the methods described herein are directed toward determining the presence of T-wave oversensing, the methods may be adapted for detecting oversensing of any lower frequency cardiac or non-cardiac signals present in an EGM or ECG signal.

Thus, a system and method for detecting oversensing have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device, comprising:

acquiring a cardiac signal comprising a plurality of cardiac events comprising first events and second events;

sensing a cardiac event in response to an amplitude of the cardiac signal exceeding a first amplitude threshold;

determining a filtered cardiac signal from the sensed cardiac signal;

determining a plurality of maxima, each maximum of the plurality of maxima being a maximum amplitude of a plurality of consecutive cardiac events;

determining a second amplitude threshold from the filtered cardiac signal as a function of the plurality of maxima;

classifying the sensed cardiac event as a first event when the sensed cardiac event corresponds to a peak amplitude of the filtered cardiac signal exceeding the second amplitude threshold; and classifying the sensed cardiac event as a second event when the sensed cardiac event corresponds to the peak amplitude of the filtered cardiac signal being less than the second amplitude threshold.

2. The method of claim 1 wherein determining the filtered cardiac signal determines the filtered signal utilizing differential filtering.

3. The method of claim 1 wherein determining the second amplitude threshold comprises:

determining multiple peaks of the filtered cardiac signal; and determining the second amplitude threshold as a function of the multiple peaks.

4. The method of claim 1 wherein the first events comprise pacing evoked events.

5. The method of claim 1 further comprising deteimining oversensing in response to the classification of the sensed cardiac event as a second event.

6. The method of claim 5 wherein determining oversensing further comprises identifying an alternating pattern of first events and second events of the plurality of cardiac events.

7. The method of claim 5 wherein determining oversensing is based, at least in part, on an event interval between a first one of the plurality of cardiac events classified as a first event and a next one of the plurality of cardiac events classified as a first event being within a predetermined event interval range.

8. The method of claim 5 wherein determining oversensing is based, at least in part, on a frequency response of one of the plurality of cardiac events being a first event and one of the plurality of cardiac events being a second event.

9. The method of claim 8 wherein the frequency response is based, at least in part, on a comparison of a first ratio of an amplitude of the cardiac signal of one of the plurality of cardiac events being the first event to an amplitude of the cardiac signal of one of the plurality of cardiac events being the second event and a second ratio of an amplitude of the filtered cardiac signal of one of the plurality of cardiac events being the first event to an amplitude of the filtered cardiac signal of one of the plurality of cardiac events being the second event.

10. The method of claim 5 wherein determining oversensing is based, at least in part, on a comparison of a first peak amplitude of one of the plurality of cardiac events being the first event to a second peak amplitude of a next one of the plurality of cardiac events being the first event.

11. The method of claim 5 wherein determining oversensing is based, at least in part, on a comparison of a first peak amplitude of one of the plurality of cardiac events being the second event to a second peak amplitude of a next one of the plurality of cardiac events being the second event.

12. The method of claim 5 wherein determining oversensing is based, at least in part, on a first interval between a first one of the plurality of cardiac events being the first event and a second one of the plurality of cardiac events being the second event being substantially equal to a second interval between the next one of the plurality of cardiac events being the first event and a fourth one of the plurality of cardiac events being the second event.

13. The method of claim 1 wherein the first events correspond to R-waves and the second events correspond to T-waves.

14. A non-transitory computer readable medium for storing a set of instructions which when implemented in an implantable medical device system cause the system to:
acquire a cardiac signal comprising a plurality of cardiac events comprising first events and second events;
sense a cardiac event in response to an amplitude of the cardiac signal exceeding a first amplitude threshold;
determine a filtered cardiac signal from the sensed cardiac signal;
determine a plurality of maxima, each maximum of the plurality of maxima being a maximum amplitude of a plurality of consecutive cardiac events;
determine a second amplitude threshold from the filtered cardiac signal as a function of the plurality of maxima;
classify the sensed cardiac event as a first event when the sensed cardiac event corresponds to a peak amplitude of the filtered cardiac signal exceeding the second amplitude threshold; and
classify the sensed cardiac event as a second event when the sensed cardiac event corresponds to the peak amplitude of the filtered cardiac signal peak being less than the second threshold.

15. An implantable medical device, comprising:
an electrode for acquiring a cardiac signal, the cardiac signal comprising a plurality of cardiac events comprising first events and second events;
a cardiac event sensing module for receiving the cardiac signal and for sensing the plurality of cardiac events in response to an amplitude of the cardiac signal exceeding a first amplitude threshold;
a filter configured to filter the cardiac signal and generate a filtered cardiac signal from the cardiac signal; and
a processor coupled to the cardiac event sensing module and the filter, wherein the processor determines a plurality of maxima, each maximum of the plurality of maxima being a maximum amplitude of a plurality of consecutive cardiac events, determines a second amplitude threshold from the filtered cardiac signal as a function of the plurality of maxima, classifies the sensed cardiac event as a first event when the sensed cardiac event corresponds to a peak amplitude of the filtered cardiac signal exceeding the second amplitude threshold, and classifies the sensed cardiac event as a second event when the sensed cardiac event corresponds to the peak amplitude of the filtered cardiac signal being less than the second amplitude threshold.

16. The implantable medical device of claim 15 wherein the filter comprises a differential filter.

17. The implantable medical device of claim 15 wherein determining the second amplitude threshold comprises:
determining multiple peaks of the filtered cardiac signal; and
determining the second amplitude threshold as a function of the multiple peaks.

18. The implantable medical device of claim 15 wherein the first events comprise pacing evoked events.

19. The implantable medical device of claim 15 wherein the processor determines oversensing in response to the classification of the sensed cardiac event as a second event.

20. The implantable medical device of claim 19 wherein determining oversensing comprises identifying an alternating pattern of first events and second events of the plurality of cardiac events.

21. The implantable medical device of claim 19 wherein the processor determines oversensing based, at least in part, on an event interval between a first one of the plurality of cardiac events classified as a first event and a next one of the plurality of cardiac events classified as a first event being within a predetermined event interval range.

22. The implantable medical device of claim 19 wherein the processor determines oversensing based, at least in part, on a frequency response of one of the plurality of cardiac events being a first event and one of the plurality of cardiac events being a second event.

23. The implantable medical device of claim 22 wherein the frequency response is based, at least in part, on a comparison by the processor of a first ratio of an amplitude of the cardiac signal of one of the plurality of cardiac events being the first event to an amplitude of the cardiac signal of one of the plurality of cardiac events being the second event and a second ratio of an amplitude of the filtered cardiac signal of one of the plurality of cardiac events being the first event to an amplitude of the filtered cardiac signal of one of the plurality of cardiac events being the second event.

24. The implantable medical device of claim 19 wherein the processor determines oversensing based, at least in part, on a comparison of a first peak amplitude of one of the plurality of cardiac events being the first event to a second peak amplitude of a next one of the plurality of cardiac events being the first event.

25. The implantable medical device of claim 19 wherein the processor determines oversensing based, at least in part, on a comparison of a first peak amplitude of one of the plurality of cardiac events being the second event to a second peak amplitude of a next one of the plurality of cardiac events being the second event.

26. The implantable medical device of claim 19 wherein the processor determines oversensing based, at least in part, on a first interval between a first one of the plurality of cardiac events being the first event and a second one of the plurality of cardiac events being the second event being substantially equal to a second interval between the next one of the plurality of cardiac events being the first event and a fourth one of the plurality of cardiac events being the second event.

27. The implantable medical device of claim 19 wherein the processor detects a cardiac rhythm of the plurality of cardiac events and rejects the cardiac rhythm detection in response to determining oversensing.

28. The implantable medical device of claim 27 further comprising a therapy delivery module controlled by the processor and wherein the processor alters a therapy delivered by the therapy delivery module in response to determining oversensing.

29. The implantable medical device of claim 15 wherein the first events correspond to R-waves and the second events correspond to T-waves.

* * * * *

UNITED STATES PATENT AND TRADEMARK OFFICE
CERTIFICATE OF CORRECTION

| | | |
|---|---|---|
| PATENT NO. | : 7,831,304 B2 | |
| APPLICATION NO. | : 11/537171 | |
| DATED | : November 9, 2010 | |
| INVENTOR(S) | : Jian Cao et al. | |

It is certified that error appears in the above-identified patent and that said Letters Patent is hereby corrected as shown below:

<u>Title Page, Item (75) Inventors:</u>
Delete "Scott R. Stanskaski," and insert in place thereof -- Scott R. Stanslanski, --.

Signed and Sealed this
Fifth Day of April, 2011

David J. Kappos
*Director of the United States Patent and Trademark Office*